United States Patent
Schulz

(10) Patent No.: US 6,555,714 B1
(45) Date of Patent: *Apr. 29, 2003

(54) INHIBITORS OF HYDROXYPHENYLPYRUVATE DIOXYGENASE AND AN ASSAY FOR IDENTIFICATION OF INHIBITORS

(75) Inventor: Arno Schulz, Eppstein (DE)

(73) Assignee: Hoechst Aktiengesellschaft, Frankfurt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 73 days.

(21) Appl. No.: 09/016,600

(22) Filed: Jan. 30, 1998

Related U.S. Application Data

(62) Division of application No. 08/462,621, filed on Jun. 5, 1995, now Pat. No. 5,786,513, which is a division of application No. 08/369,875, filed on Jan. 6, 1995, now Pat. No. 5,843,869, which is a continuation of application No. 08/200,741, filed on Feb. 23, 1994, now abandoned.

Foreign Application Priority Data

Feb. 25, 1993 (DE) .......................................... 43 05 696

(51) Int. Cl.$^7$ .............................................. C07C 49/76
(52) U.S. Cl. ........................ 568/333; 435/25; 435/184
(58) Field of Search ........................ 568/333; 435/25, 435/69.2, 184; 504/116

(56) References Cited

U.S. PATENT DOCUMENTS

| | | | |
|---|---|---|---|
| 3,954,875 A | | 5/1976 | Switherbank et al. |
| 3,983,176 A | * | 9/1976 | Yamada ...................... 568/333 |
| 3,988,300 A | | 10/1976 | Cross |
| 4,026,697 A | | 5/1977 | Cross |
| 4,511,552 A | * | 4/1985 | Cox ............................. 424/14 |
| 4,780,127 A | | 10/1988 | Michealy et al. ............. 71/103 |
| 4,910,327 A | | 3/1990 | Doehner, Jr. |
| 4,938,790 A | | 7/1990 | Smith et al. |
| 4,979,978 A | | 12/1990 | Renga et al. |
| 4,999,448 A | | 3/1991 | Smith et al. |
| 5,012,017 A | | 4/1991 | Orvik et al. |
| 5,108,486 A | | 4/1992 | Kondo et al. |
| 5,550,165 A | * | 8/1996 | Ellis et al. .................... 514/676 |
| 5,635,618 A | * | 6/1997 | Capellades et al. ......... 536/24.1 |
| 5,786,513 A | * | 7/1998 | Schulz ......................... 568/31 |
| 5,824,802 A | * | 10/1998 | Benko et al. ................ 544/140 |
| 5,843,869 A | * | 12/1998 | Schulz ........................ 504/348 |
| 5,962,690 A | * | 10/1999 | Benko et al. ................ 546/221 |
| 6,118,050 A | * | 9/2000 | Sturner et al. ............... 800/298 |
| 6,245,968 B1 | * | 6/2001 | Boudec et al. .............. 800/278 |

FOREIGN PATENT DOCUMENTS

| | | |
|---|---|---|
| EP | 133349 | 2/1985 |
| EP | 227157 | 7/1987 |
| EP | 283152 | 9/1988 |
| EP | 336494 | 10/1989 |
| EP | 384043 | 8/1990 |
| EP | 461079 | * 12/1991 |
| JP | 0100535 | 6/1985 |
| JP | 0172946 | 9/1985 |

OTHER PUBLICATIONS

Schulz A. et al. SC–0051, A 2–Benzoyl–Cyclohexane–1, 3–Dione Bleaching Herbicide . . . FEBS 318(2)162–166, Mar. 1993.*

Mac Millan J. Gibberellin Metabolism Beyond Gibberellin A12 Aldehyde 2–Oxoglutarate Couple Oxidases. British Plant Growth Regulator Group Monograph 11, 1984.*

Prisbylla M. The Novel Mechanism of Action of the Herbiciidal Triketones. Brighton Crop Protection Conference—Weeds. Vo. 2, pp. 731–738, 1993.*

Schulz A. SC–0051, A 2–Benzoyl Cyclohexane–1,3–dione Bleaching Herbicide, Is A Potent Inhibitor of the Enzyme p–Hydroxyphenylpyruvate Dioxygenase. FEBS 318(2)162–166, Mar. 1993.*

Linblad B. Radiochemical Assays for p–Hydroxyphenylpyruvate Hydroxtylase Activity in Human Liver. Clinica Chimica Acta 34:113–121, 1971.*

CA:119:22708, Abs of FEBS Lett 318(2) pp 162–6, 1993.*

Methods in Enzymology, vol. 142, "4–Hydroxyphenylpyruvate Dioxygenase from Human Liver" by Lindstedt et al., pp. 139–141 (1987).

Methods in Enzymology, vol. 142, "4–Hydroxyphenylpyruvate Dioxygenase from Pseudomonas" by Lindstedt et al., pp. 143–148 (1987).

(List continued on next page.)

*Primary Examiner*—Ralph Gitomer
(74) *Attorney, Agent, or Firm*—Frommer Lawrence & Haug LLP

(57) ABSTRACT

Disclosed and claimed is an assay for identifying potential inhibitors of p-hydrophenylpyruvate dioxygenases (HPPD) from plants, in which an enriched HPPD from plants is incubated with a test substrate to be examined and the enzymatic activity of the enzyme is determined in comparison with the activity of the uninhibited enzyme. Also disclosed and claimed is a method of using the inhibitors of HPPD of a plant identified by the assay, such as their use as herbicides. Further disclosed and claimed are novel herbicidal active substances, including those of the formula (I)

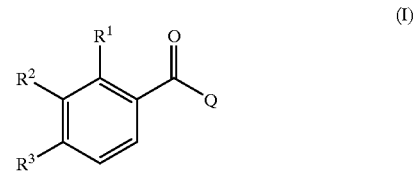

(I)

which were found using the assay method according to the invention.

4 Claims, No Drawings

OTHER PUBLICATIONS

Elsevier/North–Holland Biomedical Press, FEBS Letters, vol. 104, No. 2, "Conversion of 4–Hydroxyphenylpyruvic Acid into Homogentistic Acid at the Thylakoid Membrane" by Löffelhardt et al., pp. 332–334, Aug. 1979.

Clinical Chimica Acta, vol. 34, "Radiochemical Assays for p–Hydrophenylpyruvate Hydroxylase Activity in Human liver", by Bengt Lindblad, pp. 113–121 (1971).

Planta 155, "The Formation of Homogentisate in the Biosynthesis of Tocopherol and Plastoquinone in Spinach Chloroplasts" by Fiedler et al., pp. 511–515 (1982).

Grompe M. et al., Nat. Genet., 10(4): 453–60 (1995).

Abstract No. 92:17785g, Sadunishvili, T.A., et al., Kinetic properties of malate dehydrogenase from lemon [tree leaves], *Izv. Akad. Nauk. Gruz. SSR, Ser. Biol.,* 5(4), 327–33 (1979).

Abstract No. 92:17781c, Maruyama, Etsuko, et al., Homogentisic acid formation by p–hydroxyphenylpyruvate hydroxylase in bamboo shoots, *Kaseigaku Zasshi,* 30(7), 603–7 (1979).

* cited by examiner

INHIBITORS OF HYDROXYPHENYLPYRUVATE DIOXYGENASE AND AN ASSAY FOR IDENTIFICATION OF INHIBITORS

This application is a divisional of U.S. application Ser. No. 08/462,621, filed Jun. 5, 1995, now U.S. Pat. No. 5,786,513, which in turn is a divisional of application Ser. No. 08/369,875, filed Jan. 6, 1995, now U.S. Pat. No. 5,843,869, which in turn is a continuation of application Ser. No. 08/200,741, filed Feb. 23, 1994, now abandoned.

p-Hydroxyphenylpyruvate dioxygenase (HPPD; p-hydroxyphenylpyruvate: oxygen oxidoreductase, EC 1.13.11.27) in plant tissues is an enzyme central to the biosynthesis of the quinoid compounds derived from the amino acid tyrosine, such as plastoquinones or tocopherols. During the biosynthesis of quinone, tyrosine is first transaminated by a transaminase to give p-hydroxyphenylpyruvate, which is then decarboxylated and hydroxylated by the enzyme HPPD in a complex sequence. The product of this reaction is homogentisic acid. These first two steps of quinone biosynthesis can analogously also be detected in animal tissues and microorganisms. While, in plants, the homogentisic acid formed can be reacted to give plastoquinones and tocopherols, however, it is an intermediate in the catabolism of the amino acid tyrosine in animals and microorganisms. Plastoquinones and tocopherols are essential structures for plants. Inhibitors of the biosynthesis of plastoquinones and tocopherols should therefore be potential herbicides.

Catabolic p-hydroxyphenylpyruvate dioxygenases have previously been purified and characterized from animal tissues (Lindstedt, S. and Odelhög, B. (1987) Meth. Enzymol. 142, 139–142) and microorganisms (Lindstedt, S. and Odelhög, B. (1987) Meth. Enzymol. 142, 143–148). (Anabolic) p-hydroxyphenylpyruvate dioxygenases from plants, in contrast, have been described in the literature (Fiedler, E., Soll, J. and Schultz, G. (1982) Planta 155, 511–515), but no method for enriching the enzyme has been described to date.

Specifically, there has been no information to date in the literature on simple methods of measuring the plant enzyme which, of course, are indispensable for purification of the enzyme and detecting inhibitors of the enzyme.

The method described by Fiedler et al. is relatively complicated and does not allow the quantitative assays to be carried out which are required for identifying potential herbicides.

What follows describes a method for enriching the anabolic p-hydroxyphenylpyruvate dioxygenases from plant tissues and a method by means of which the enzymatic activity of the enzyme can be measured in a simple manner without complete purification of the enzyme being necessary.

The invention therefore relates to:
A method for enriching an anabolic p-hydroxyphenylpyruvate dioxygenase from plant cells, which comprises isolating the enzyme directly from a buffer in which the cells were homogenized.

The invention furthermore relates to an assay system for identifying inhibitors of p-hydroxyphenylpyruvate dioxygenase from plants, which comprises incubating an enriched HPPD from plants with a test substrate to be examined and determining the enzymatic activity of the enzyme in comparison with the activity of the uninhibited enzyme.

In particular, the invention relates to a method in which the plant tissue or cells are homogenized in extraction buffer, the extract is filtered, the supernatant is subjected to fractional ammonium sulfate precipitation, and the precipitate formed is redissolved.

Suitable extraction buffers are the extraction buffers conventionally used for plant cells, in particular the extraction buffer which is composed as follows:
20 mM phosphate buffer pH 7.0;
0.14 M KCl;
0.1 mg/ml glutathione and
1% of insoluble polyvinylpyrrolidone.

Suitable test substrates are all compounds which are potential HPPD inhibitors. These potential inhibitors are preferably stucturally similar to the natural substrate of HPPD. However, other substances which do not bind in the active center of the enzyme, but which inhibit the enzyme in a different manner, can also be used.

The enzymatic activity can be determined by means of the methods known from the literature (see Bergmeyer, H. U., Methoden der enzymatischen Analyse [Methods in enzymatic analysis], Volumes 1 and 2, Verlag Chemie, Weinheim, (1974) and Suelter, C. H., Experimentelle Enzymologie: Grundlagen für die Laborpraxis [Experimental Enzymology: Fundamentals of Laboratory Practice], Fischer Stuttgart (1990)).

A modified form of the method for measuring catabolic HPPDs from human liver has been described by Lindblad (Lindblad, B. (1971) Clin. Chim. Acta 34, 113–121). Endpoint measurements are used in this case for detecting $^{14}C-CO_2$, which is liberated from $^{14}C$-p-hydroxyphenylpyruvate by the enzymatic activity of HPPD. If HPPD inhibitors are present in the reaction batch, the enzyme reaction and hence the liberation of $CO_2$ are suppressed. This assay method allows inhibitors of the enzyme to be found.

It is preferred to carry out the assay in such a way that the enzymatic activity of the HPPD is started up after preincubation of the enriched HPPD with the potential inhibitor by adding the radiolabeled $^{14}C$-p-hydroxyphenylpyruvate, stopping the reaction after a suitable incubation time, and measuring the enzymatic activity indirectly via the radioactivity which has been liberated.

It is self-evident that the assay according to the invention can also be carried out with the purified enzyme. The enzyme can be further enriched in a manner known per se by means of chromatography on anion exchangers, such as, for example, Q-Sepharose, by Pharmacia, followed by gel permeation chromatography, such as, for example, Superdex 200, by Pharmacia, but this is not necessary for carrying out the assay.

Surprisingly, a new class of HPPD inhibitors has now also been identified using this assay system. They are herbicides from the group of the 2-benzoylcyclohexane-1,3-diones. This is surprising since an entirely different mechanism of action is suggested in the literature for this compounds class on the basis of its herbicidal symptoms (they lead to bleaching of the plants). It is assumed that, analogously to other bleaching herbicides, they inhibit phytoene desaturase (Soeda, T. and Uchida, T. (1987) Pestic. Biochem. Physiol. 29, 35–42; Mayonada, D. J., Hatzios, K. K., Orcutt, D. M. and Wilson, H. P. (1989) Pestic. Biochem. Physiol. 35, 138–145). It was possible to demonstrate that this compounds class, while not inhibiting phytoene desaturase, does inhibit HPPD; under the assay conditions, $4.5 \times 10^{-8}$ M 2-(2-chloro-4-methanesulfonylbenzoyl)-1,3-cyclohexanedione (SC-0051, a typical representative of this class of herbicides) showed a 50% inhibition on the anabolic plant HPPD from maize (which corresponds to the IC50 value). Bleaching herbicides which have a different structure do not, in contrast, inhibit HPPD, but inhibit the enzyme phytoene desaturase.

However, the method according to the invention allows not only the activity of known herbicides to be demonstrated at the molecular level, but also novel, previously unknown herbicidal active substances which inhibit HPPD to be identified.

The invention therefore also relates to the novel herbicidal active substances found by the assay method according to the invention.

The invention therefore also relates to compounds of the formula (I)

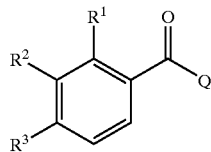

in which
R$^1$ is H, halogen, OH, alkoxy, CN, NO$_2$ or-haloalkyl,
R$^2$ is H, halogen, OH, alkyl, alkoxy, haloalkyl, haloalkoxy or (alkoxy)-carbonyl,
R$^3$ is H, halogen, OH, CN, NO$_2$, haloalkyl, haloalkoxy or R$^4$S(O)$_m$—, where R$^4$ is alkyl and m is zero, one or two,
Q is a radical selected from the group of the formula

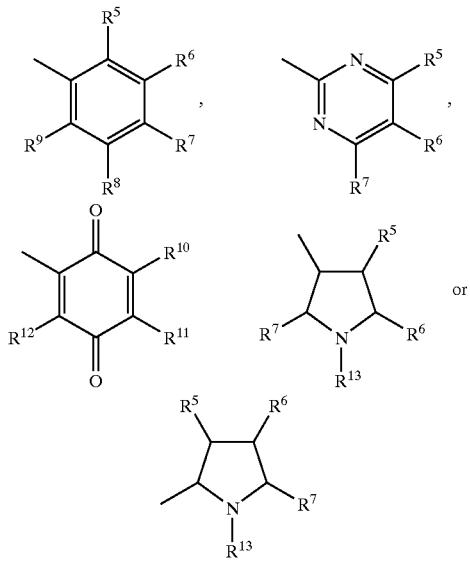

where
R$^5$, R$^6$, R$^7$, R$^8$ and R$^9$ independently of one another are H, halogen, OH, CN, NO$_2$, SO$_3$H, SO$_3$R$^4$, SO$_2$NR$^{14}$R$^{15}$, COOH, COOR$^4$, CONR$^{14}$R$^{15}$, O—COOR$^4$, O—COR$^4$, -alkyl, alkoxy, haloalkyl or haloalkoxy,
R$^{10}$, R$^{11}$ and R$^{12}$ independently of one another are H, halogen, alkyl, alkoxy, haloalkyl or haloalkoxy,
R$^{13}$ is H, phenylsulfonyl, alkylsulfonyl or alkylcarbonyl, and
R$^{14}$ and R$^{15}$ independently of one another are H, alkyl, aryl or benzyl.

In the formula (I), the radicals alkyl, alkoxy, haloalkyl and haloalkoxy can in each case be straight-chain or branched.

Alkyl radicals are, for example, methyl, ethyl, n- or i-propyl or n-, i-, t- or 2-butyl. Aryl embraces aromatic and heteroaromatic radicals, such as, for example, phenyl, 2- or 3-naphthyl or 2-, 3- or 4-pyridyl. Halogen is fluorine, chlorine, bromine or iodine.

The use according to the invention of compounds of the formula (I) in which
R$^1$ is H, halogen, OH, C$_1$–C$_3$-alkoxy, CN, NO$_2$ or C$_1$–C$_3$-haloalkyl,
R$^2$ is H, halogen, OH, C$_1$–C$_3$-alkyl, C$_1$–C$_3$-alkoxy, C$_1$–C$_2$-haloalkyl, C$_1$–C$_2$-haloalkoxy or (C$_1$–C$_2$-alkoxy)-carbonyl,
R$^3$ is H, halogen, OH, CN, NO$_2$, C$_1$–C$_3$-haloalkyl, C$_1$–C$_2$-haloalkoxy or R$^4$S(O)$_m$—, where R$^4$ is C$_1$–C$_2$-alkyl and m is zero, one or two,
Q is a radical selected from the group of the formula

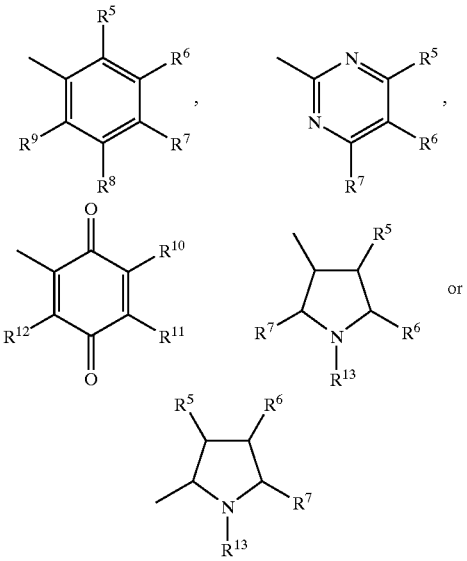

where
R$^5$, R$^6$, R$^7$, R$^8$ and R$^9$ independently of one another are H, halogen, OH, CN, NO$_2$, SO$_3$H, SO$_3$R$^4$, SO$_2$NR$^{14}$R$^{15}$, COOH, COOR$^4$, CONR$^{14}$R$^{15}$, O—COOR$^4$, O—COR$^4$, C$_1$–C$_4$-alkyl, C$_1$–C$_2$-alkoxy, C$_1$–C$_3$-haloalkyl or C$_1$–C$_2$-haloalkoxy,
R$^{10}$, R$^{11}$ and R$^{12}$ independently of one another are H, halogen, C$_1$–C$_3$-alkyl, C$_1$–C$_2$-alkoxy, C$_1$–C$_3$-haloalkyl or C$_1$–C$_2$-haloalkoxy,
R$^{13}$ is H, phenylsulfonyl, C$_1$–C$_2$-alkylsulfonyl or C$_1$–C$_2$-alkylcarbonyl, and
R$^{14}$ and R$^{15}$ independently of one another are H, C$_1$–C$_4$-alkyl, phenyl or benzyl,
is of particular interest.

Preferred is the use according to the invention of compounds of the formula (I) with at least one of the following characteristics:
R$^1$ is preferably hydrogen, hydroxyl, fluorine, chlorine, bromine, cyano, nitro, methoxy, ethoxy, difluoromethyl, trifluoromethyl, chloromethyl, trichloromethyl, 2,2,2-trifluoroethyl or pentafluoroethyl,
R$^2$ is preferably hydrogen, fluorine, chlorine, hydroxyl, propyl, ethyl, methyl, methoxy, ethoxy, difluoromethyl, trifluoromethyl, difluoromethoxy, trifluoromethoxy, methoxycarbonyl or ethoxycarbonyl,
R$^3$ is preferably hydrogen, hydroxyl, fluorine, chlorine, bromine, cyano, nitro, difluoromethyl, trifluoromethyl, chloromethyl, trichloromethyl, 2,2,2-tri fluoroethyl, pentafluoroethyl, difluoromethoxy, trifluoromethoxy, methylsulfonyl or ethylsulfonyl;

Q is preferably the radical

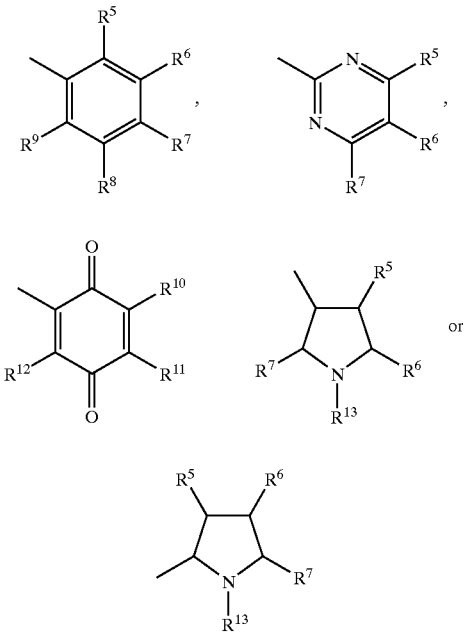

where

R⁵, R⁶, R⁷, R⁸ and R⁹ preferably and independently of one another are hydrogen, fluorine, chlorine, bromine, cyano, nitro, hydroxyl, hydroxysulfonyl, ethoxysulfonyl, ethylaminosulfonyl, methylaminosulfonyl, carboxyl, ethoxycarbonyl, methoxycarbonyl, ethylaminocarbonyl, methylaminocarbonyl, ethoxycarbonyloxy, methoxycarbonyloxy, methylcarbonyloxy, t-butyl, i-propyl, propyl, ethyl, methyl, difluoromethyl, trifluoromethyl, chloromethyl, trichloromethyl, methoxy, ethoxy, difluoromethoxy or trifluoromethoxy, R¹⁰, R¹¹ and R¹² preferably and independently of one another are hydrogen, fluorine, chlorine, bromine, ethyl, methyl, difluoromethyl, trifluoromethyl, chloromethyl, trichloromethyl, methoxy, ethoxy, difluoromethoxy or trifluoromethoxy, R¹³ is preferably hydrogen, phenylsulfonyl, methylsulfonyl, ethylsulfonyl, methylcarbonyl or ethylcarbonyl, and R¹⁴ and R¹⁵ preferably and independently of one another are hydrogen, butyl, propyl, ethyl, methyl or benzyl.

The uses according to the invention of compounds of the formula (I) with a combination of the abovementioned preferred characteristics are also preferred.

The compounds of the abovementioned formula (I) can be prepared, for example, by reacting aromatic carboxylic acid chlorides of the formula (II)

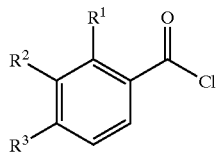

in which the substituents R¹, R² and R³ are as defined under formula (I), with aromatic or heteroaromatic compounds of the type H—Q, in which Q is as defined under formula (I), in an inert solvent in the presence of a Lewis acid.

The compounds (I) are preferably prepared in aprotic solvents, in particular in halogenated hydrocarbons, such as, for example, dichloromethane, trichloromethane, 1,2-dichloromethane or 1,1,2,2-tetrachloroethane, at from −20° C. up to the boiling point of the reaction mixture, in particular at from room temperature to 50° C., the reaction being carried out in the presence of a catalytically to stoichiometrically employed amount of Lewis acid, such as, for example, aluminum chloride, titanium tetrachloride or boron trifluoride.

A. PREPARATION EXAMPLES a) 3-(2,4-Dichlorobenzoyl)-1-phenylsulfonylpyrrole (Table 1, Example No. 150)

4.0 ml of 2,4-dichlorobenzoyl chloride and 4.00 g of aluminum chloride are stirred for 10 minutes at room temperature in 50 ml of 1,2-dichloroethane. A solution of 5.10 g of phenylsulfonylpyrrole in 20 ml of 1,2-dichloroethane is added dropwise to the mixture, and this is stirred for 2 hours at room temperature. The mixture is poured into ice-water and extracted using dichloromethane. The organic phase is dried and evaporated. Recrystallization of the residue from a mixture of ethyl acetate and petroleum ether gives 8.3 g (89% of theory) of 3-(2,4-dichlorobenzoyl)-1-phenylsulfonylpyrrole in the form of white crystals with a melting point of 122° C.

b) 2,5'-Dichloro-2'-hydroxy-3'-methyl-4-methylsulfonylbenzophenone (Table 1, Example No. 100)

5.06 g of 2-chloro-4-methylsulfonylbenzoyl chloride are added in portions at room temperature to a mixture of 2.85 g of 4-chloro-2-methylphenol and 5.40 g of aluminum chloride in 100 ml of 1,1,2,2-tetra chloroethane, and the mixture is subsequently refluxed for 7 hours. When cold, the reaction mixture is poured onto 200 g of ice and 500 ml of concentrated hydrochloric acid. The organic phase is separated off, and the aqueous phase is extracted twice using 50 ml of dichloromethane. The combined organic phases are washed until neutral, dried over magnesium sulfate and evaporated. Recrystallization from a mixture of ethyl acetate and diisopropyl ether gives 4.2 g (60% of theory) of 2,5'-dichloro-2'-hydroxy-3'-methyl-4-methylsulfonylbenzophenone in the form of colorless crystals with a melting point of 175–180° C.

c) 2-(2,4-Dichlorobenzoyl)-1,4-quinone (Table 1, Example No. 91)

A solution of 2.49 g of 2-(2,4-dichlorobenzoyl)-1,4-dihydroxybenzene in 20 ml of glacial acetic acid is added dropwise at 10° C. in the course of 3 minutes to a solution of 1.60 g of sodium dichromate in 2 g of concentrated sulfuric acid and 60 ml of water. The reaction mixture is stirred vigorously for a further 30 minutes at 10–15° C. and then filtered. The residue is washed with water until free from acid and recrystallized from diisopropyl ether. 1.74 g (70% of theory) of 2-(2,4-dichlorobenzoyl)-1,4-quinone are obtained in the form of yellowish-orange crystals with a melting point of 100° C.

d) 2,2',4'-Trichloro-6'-hydroxy-4-methylsulfonylbenzophenone (Table 1, Example No. 183)

3.00 g of 2-chloro-4-methylsulfonylbenzoyl chloride are added in portions at room temperature to a mixture of 1.97 g of 3,5-dichlorophenone and 3.23 g of aluminum chloride in 50 ml of 1,1,2,2-tetra chloroethane, and the mixture is subsequently refluxed for 7 hours. When cold, the reaction mixture is poured onto 100 g of ice and 20 ml of concentrated hydrochloric acid. The organic phase is removed, and the aqueous phase is extracted twice using 50 ml of dichloromethane. The combined organic phases are washed until neutral and subsequently extracted three times using in each case 25 ml of 2 N sodium hydroxide solution. The combined alkaline extracts are brought to a pH of 2 using concentrated hydrochloric acid. The precipitate is filtered off, washed with water until neutral and dried. This gives 3.194 g (70% of theory) of 2,2',4'-trichloro-6'-hydroxy-4-methylsulfonylbenzophenone in the form of colorless crystals with a melting point of 123–126° C.

The compounds listed in Table 1 are obtained analogously to the preparation examples described above.

TABLE 1

Compounds of the formula (I) according to the invention (I)

| No. | $R^1$ | $R^2$ | $R^3$ | Q | M.p. [° C.] | $IC_{50}$ |
|---|---|---|---|---|---|---|
| 1 | Cl | H | $NO_2$ | (2,3-dichloro-6-methylphenol) | 135–139 | $<10^{-9}$ |
| 2 | Cl | $CH_3$ | $SO_2CH_3$ | (4,6-dichloro-2-methylpyrimidine) | | |
| 3 | Cl | H | $OCF_2H$ | (2-methyl-5-chloro-$SO_2NHCH_3$-phenyl) | | |
| 4 | Br | H | CN | (methyl-$CF_2H$-$CH_3$-benzoquinone) | | |
| 5 | Br | H | $NO_2$ | (2-methyl-4-$OCF_2H$-6-chloropyrimidine) | | |

TABLE 1-continued

Compounds of the formula (I) according to the invention (I)

| No. | R¹ | R² | R³ | Q | M.p. [°C.] | IC$_{50}$ |
|-----|------|-------|--------------------|---|------------|-----------|
| 6 | Cl | OC$_2$H$_5$ | SO$_2$CH$_3$ | 2,6-dichloro-4-(trifluoromethyl)phenyl (with methyl) | | |
| 7 | Cl | H | SO$_2$CH$_3$ | 2,6-dihydroxy-3-methylphenyl | 228 | 5.7 × 10$^{-7}$ |
| 8 | F | OH | CH$_2$CF$_3$ | 2-ethyl-3-methyl-4-chloro-6-(methoxycarbonyl)phenyl | | |
| 9 | NO$_2$ | F | CH$_2$Cl | 2,3-dichloro-5-methyl-1,4-benzoquinon-6-yl | | |
| 10 | Cl | H | SO$_2$CH$_3$ | 2,6-dihydroxy-3-methyl-5-methylphenyl | 225 (decomp.) | 1.8 × 10$^{-7}$ |
| 11 | OC$_2$H$_5$ | CF$_2$H | SO$_2$CH$_3$ | 1-acetyl-3-chloro-4-methylpyrrol-2-yl | | |
| 12 | OCH$_3$ | H | Br | 2-(trifluoromethyl)-3-methyl-4-fluoro-6-(trifluoromethoxy)phenyl | | |

TABLE 1-continued

Compounds of the formula (I) according to the invention (I)

| No. | R¹ | R² | R³ | Q | M.p. [° C.] | IC$_{50}$ |
|---|---|---|---|---|---|---|
| 13 | OH | Cl | Cl | 2,4,5-trimethoxyphenyl | 98–100 | <10⁻⁹ |
| 14 | Cl | H | SO$_2$CH$_3$ | 2,5-dihydroxyphenyl | 267 (decomp.) | |
| 15 | F | COOCH$_3$ | CH$_2$CF$_3$ | 2-(CF$_2$H)-6-hydroxy-4-chlorophenyl | | |
| 16 | Cl | H | Cl | 2,6-dihydroxyphenyl | 147 | |
| 17 | Cl | Cl | Br | 3-chloro-4-methyl-1-acetylpyrrol-2-yl | | |
| 18 | CN | F | CH$_2$Cl | 2,6-dichloro-4-(CF$_3$)phenyl | | |
| 19 | OH | Cl | Cl | 4-tert-butylphenyl | 95–101 | |

TABLE 1-continued

Compounds of the formula (I) according to the invention

| No. | R¹ | R² | R³ | Q | M.p. [°C.] | IC$_{50}$ |
|---|---|---|---|---|---|---|
| 20 | CH$_2$Cl | OCH$_3$ | NO$_2$ | 3,4,5-trihydroxyphenyl | | |
| 21 | Br | Cl | Cl | 3-bromo-5-(N-methylsulfamoyl)phenyl | | |
| 22 | OH | Cl | Cl | 2-chlorophenyl | 126–128 | |
| 23 | H | H | SO$_2$CH$_3$ | 2,6-dihydroxyphenyl | 224 | |
| 24 | CH$_2$CF$_3$ | COOCH$_3$ | Cl | 2,5-dichloro-3-(methoxycarbonyl)phenyl | | |
| 25 | F | Cl | SO$_2$CH$_3$ | 2-(difluoromethyl)-4-chloro-6-hydroxyphenyl | | |
| 26 | OH | Cl | Cl | 2-methylphenyl | 97–100 | |

TABLE 1-continued

Compounds of the formula (I) according to the invention

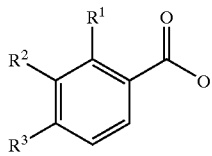

(I)

| No. | R¹ | R² | R³ | Q | M.p. [° C.] | IC$_{50}$ |
|---|---|---|---|---|---|---|
| 27 | NO$_2$ | H | CF$_3$ | (2,3-dichloro-5-methyl-1,4-benzoquinone) | | |
| 28 | Br | Cl | OCF$_2$ | (2,3-dichloro-5-methyl-1,4-benzoquinone) | | |
| 29 | Cl | H | NO$_2$ | (2,6-dihydroxy-3-methyl-... with CH$_3$) | 192 | |
| 30 | NO$_2$ | H | Cl | (hydroxy, Cl, COOCH$_3$ substituted phenyl) | | |
| 31 | CCl$_3$ | F | SO$_2$CH$_3$ | (hydroxy, Cl, COOCH$_3$ substituted phenyl) | | |
| 32 | Cl | H | NO$_2$ | (2,6-dihydroxyphenyl, methyl) | 178 | |
| 33 | NO$_2$ | Cl | Cl | (2,6-dichloro-4-trifluoromethylphenyl, methyl) | | |

TABLE 1-continued

Compounds of the formula (I) according to the invention (I)

| No. | R¹ | R² | R³ | Q | M.p. [° C.] | IC$_{50}$ |
|-----|-----|-----|-----|---|-------------|-----------|
| 34 | OH | Cl | Cl | (phenyl) | 124–128 | |
| 35 | Cl | H | Cl | (2,5-dihydroxy-methylphenyl) | 135 | < × 10$^{-9}$ |
| 36 | Cl | Cl | CN | (3,5-dichloro-4-methyl-phenyl with COOC$_2$H$_3$) | | |
| 37 | Cl | H | SO$_2$CH$_3$ | (4-chloro-3-(SO$_3$—CH$_3$)-methylphenyl) | | |
| 38 | Cl | H | SO$_2$CH$_3$ | (2-hydroxy-3,5-dimethoxy-6-methylphenyl) | 147 | |
| 39 | Cl | COOCH$_3$ | SO$_2$CH$_3$ | (2-OCF$_3$-3-SO$_3$H-methylphenyl) | | |
| 40 | Cl | H | Cl | (2,5-dimethoxy-methylphenyl) | 86 | 9.7 × 10$^{-7}$ |

TABLE 1-continued

Compounds of the formula (I) according to the invention

| No. | R$^1$ | R$^2$ | R$^3$ | Q | M.p. [°C.] | IC$_{50}$ |
|---|---|---|---|---|---|---|
| 41 | Cl | C$_3$H$_7$ | SO$_2$CH$_3$ | 3-methyl-2-(OCF$_3$)-phenyl-6-SO$_3$H | | |
| 42 | OH | Cl | Cl | 2-methyl-5-methylphenyl (p-tolyl variant) | 134–136 | 3.5 × 10$^{-6}$ |
| 43 | Cl | H | Cl | 2-methyl-3,5-dimethoxy-6-methoxy phenyl | 103 | 3.5 × 10$^{-6}$ |
| 44 | H | OCF$_3$ | F | 3-methyl-5-bromo-phenyl-SO$_2$NHCH$_3$ | | |
| 45 | NO$_2$ | H | Cl | 2-methyl-1H-pyrrol-yl | 125 | |
| 46 | Cl | CH$_3$ | CF$_2$H | 2-OCH$_3$-3-methyl-6-Cl-phenyl-COOCH$_3$ | | |
| 47 | Cl | H | SO$_2$CH$_3$ | 2-methyl-3,5-dimethoxy-6-methoxy phenyl | 163–166 | 5.7 × 10$^{-6}$ |

TABLE 1-continued
Compounds of the formula (I) according to the invention
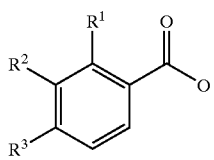
(I)
| No. | R¹ | R² | R³ | Q | M.p. [° C.] | IC$_{50}$ |
|---|---|---|---|---|---|---|
| 48 | F | COOCH$_3$ | OCF$_2$H | 2-Cl, 3,5-dimethyl, 6-SO$_3$H phenyl | | |
| 49 | Cl | H | Cl | 2,4,5-trimethoxy phenyl | 99 | |
| 50 | OH | Cl | Cl | 2,6-difluoro phenyl | 98–103 | |
| 51 | CH$_2$Cl | C$_3$H$_7$ | SO$_2$CH$_3$ | trimethylbenzoquinone | | |
| 52 | NO$_2$ | OH | Br | 3,4-dichloro-5-COOCH$_3$ phenyl | | |
| 53 | CF$_3$ | H | Cl | 3-Cl, 2-Br, 6-COOC$_2$H$_5$ phenyl | | |

TABLE 1-continued

Compounds of the formula (I) according to the invention (I)

| No. | R¹ | R² | R³ | Q | M.p. [°C.] | IC$_{50}$ |
|---|---|---|---|---|---|---|
| 54 | Cl | H | Cl | (2-methyl-3,5-dimethoxy-phenol) | | |
| 55 | Cl | Cl | Cl | (2-chloro-3,5-dimethyl-benzenesulfonic acid) | | |
| 56 | OH | Cl | Cl | (4-ethylphenyl, methyl) | 64–65 | $5.0 \times 10^{-8}$ |
| 57 | Br | H | OCF$_3$ | (3-chloro-5-methylphenol) | | |
| 58 | F | CH$_3$ | F | (2-CF$_2$H-4-chloro-6-methylphenol) | | |
| 59 | Br | Cl | Cl | (4-F, 3-methyl, 2-OH, COOC$_2$H$_5$ substituted phenyl) | | |
| 60 | Cl | H | SO$_2$CH$_3$ | (2-methyl-1,3,5-trihydroxybenzene) | 165 | |

TABLE 1-continued

Compounds of the formula (I) according to the invention (I)

| No. | R¹ | R² | R³ | Q | M.p. [° C.] | IC$_{50}$ |
|-----|-----|-----|-----|-----|-----|-----|
| 61 | NO$_2$ | H | OCF$_2$H | 3-methyl-5-(OCF$_3$)benzoic acid | | |
| 62 | CF$_3$ | Cl | Cl | 3,5-dichloro-5-hydroxytoluene derivative | | |
| 63 | Cl | H | SO$_2$CH$_3$ | 2-methyl-3,5,6-trihydroxybenzene | 227 | |
| 64 | CCl$_3$ | H | Cl | 3-methyl-5-(OCF$_3$)benzoic acid | | |
| 65 | Cl | H | CF$_3$ | 2-fluoro-5-methylacetophenone derivative | | |
| 66 | Cl | H | SO$_2$CH$_3$ | 2-methyl-3,4,5-trihydroxybenzene | 228 | |
| 67 | Cl | CH$_3$ | OCF$_2$H | 4-methyl-5-hydroxy-2-methoxybenzonitrile | | |

TABLE 1-continued

Compounds of the formula (I) according to the invention (I)

| No. | R¹ | R² | R³ | Q | M.p. [° C.] | IC$_{50}$ |
|---|---|---|---|---|---|---|
| 68 | Cl | CF$_3$ | OCF$_2$H | 2-Cl-3-Br-5-CH$_3$-phenyl | | |
| 69 | Cl | H | SO$_2$CH$_3$ | 2-Cl-3-(OCH(COOCH$_3$))-6-CN-phenyl | | |
| 70 | Cl | H | SO$_2$CH$_3$ | 2-OH-4-NH$_2$-phenyl | 240 (decomp.) | 4.0 × 10$^{-8}$ |
| 71 | OCH$_3$ | COOCH$_3$ | SO$_2$CH$_3$ | 2-OH-3-Br-5-OCH$_3$-phenyl | | |
| 72 | Cl | H | SO$_2$C$_2$H$_5$ | 3,5-dimethyl-1,4-benzoquinon-2-yl | | |
| 73 | CF$_3$ | CH$_3$ | Cl | 2-Cl-4-CH$_3$-5-OH-SO$_2$NHCH$_3$-phenyl | | |
| 74 | Cl | H | SO$_2$CH$_3$ | 3-methyl-1H-pyrrol-? | 151–153 | |

TABLE 1-continued

Compounds of the formula (I) according to the invention

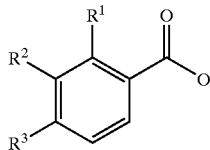

(I)

| No. | R¹ | R² | R³ | Q | M.p. [°C.] | IC$_{50}$ |
|---|---|---|---|---|---|---|
| 75 | F | OCF$_3$ | Cl | (3-hydroxy-4-methyl-phenyl-SO$_2$NHCH$_3$) | | |
| 76 | Cl | CF$_3$ | Cl | (tetramethyl-benzoquinone) | | |
| 77 | H | COOC$_2$H$_5$ | SO$_2$CH$_3$ | (2,3-dimethyl-4-ethoxy-6-nitro-phenyl) | | |
| 78 | Cl | H | SO$_2$CH$_3$ | (2,5-dichloro-4-methyl-3-(OCF$_2$H)-pyrrole) | | |
| 79 | NO$_2$ | H | Cl | (2-methyl-1-(phenylsulfonyl)-pyrrole) | 160–162 | |
| 80 | F | Cl | Cl | (4-fluoro-3-methyl-2-(CF$_3$)-6-methoxy-phenyl) | | |
| 81 | OCH$_3$ | COOCH$_3$ | SO$_2$CH$_3$ | (2-bromo-3,6-dihydroxy-4-methyl-phenyl) | | |

TABLE 1-continued

Compounds of the formula (I) according to the invention (I)

| No. | R¹ | R² | R³ | Q | M.p. [° C.] | IC$_{50}$ |
|-----|----|----|----|----|-------------|-----------|
| 82 | Cl | Cl | OH | *4-methylphenyl-CH(CH₃)-* | 137–139 | |
| 83 | Cl | Cl | CF₃ | *2-methyl-6-bromo-4-methoxyphenol* | | |
| 84 | F | C₂H₅ | Cl | *3-chloro-4-OCF₂H-5-methyl-2-chloro-pyrrole* | | |
| 85 | OCF₂H | Cl | Cl | *3-OCF₂H-5-methyl-pyrrole* | | |
| 86 | Cl | H | SO₂CH₃ | *2-methyl-1,3,5-triacetoxyphenyl* | 157 | |
| 87 | Cl | H | SO₂CH₃ | *2,5-dimethoxy-3-methylphenyl* | 108 | $2.4 \times 10^{-7}$ |

TABLE 1-continued

Compounds of the formula (I) according to the invention (I)

| No. | R¹ | R² | R³ | Q | M.p. [° C.] | IC$_{50}$ |
|---|---|---|---|---|---|---|
| 88 | Cl | H | SO$_2$CH$_3$ | *(3-methyl-4-hydroxy-benzoic acid)* | 254–256 | $7.0 \times 10^{-8}$ |
| 89 | CF$_2$H | Cl | Cl | *(2,6-dichloro-4-trifluoromethyl-phenyl)* | | |
| 90 | Br | H | SO$_2$ | *(3-chloro-2-methyl-6-(difluoromethoxy)-phenyl with CH$_3$)* | | |
| 91 | Cl | H | Cl | *(2-methyl-benzoquinone)* | 100 | $1.8 \times 10^{-8}$ |
| 92 | Cl | C$_2$H$_5$ | CF$_3$ | *(3-bromo-2-(difluoromethoxy)-6-(methylsulfonylamino)-phenyl)* | | |
| 93 | F | F | F | *(2,4-dichloro-6-(N-methylcarbamoyl)-phenyl)* | | |
| 94 | Cl | Cl | OH | *(2,6-difluorophenyl)* | 149–152 | |

TABLE 1-continued

Compounds of the formula (I) according to the invention (I)

| No. | R¹ | R² | R³ | Q | M.p. [° C.] | IC$_{50}$ |
|-----|-----|-----|-----|---|-------------|-----------|
| 95 | OH | Cl | Cl | 2,6-difluoro-3-methylphenyl | 118–121 | |
| 96 | OC$_2$H$_5$ | Cl | CF$_3$ | 3-bromo-2,4-dihydroxy-6-methylphenyl | | |
| 97 | Cl | H | SO$_2$CH$_3$ | 4-hydroxy-3-methylphenyl carboxylate | 180 (decomp.) | $6.0 \times 10^{-8}$ |
| 98 | CN | F | F | 3-chloro-5-(N-methylsulfamoyl)methylphenyl | | |
| 99 | Cl | H | SO$_2$CH$_3$ | 5-chloro-2-hydroxy-3-methyl-N-methylbenzamide | | |
| 100 | Cl | H | SO$_2$CH$_3$ | 4-chloro-2-hydroxy-3,5-dimethylphenyl | 175–180 | $6.2 \times 10^{-9}$ |
| 101 | Cl | H | SO$_2$CH$_3$ | 4-chloro-2-hydroxy-3-methylphenyl | 183 | $<10^{-9}$ |

TABLE 1-continued

Compounds of the formula (I) according to the invention (I)

| No. | R¹ | R² | R³ | Q | M.p. [° C.] | IC$_{50}$ |
|-----|----|----|----|----|-------------|-----------|
| 102 | Cl | OCH$_3$ | NO$_2$ | 2-Cl, 5-SO$_3$—CH$_3$ phenyl | | |
| 103 | F | Cl | Cl | 2-Cl, 3-CH$_3$, 4-OCF$_2$H phenyl | | |
| 104 | Cl | H | Cl | 2-OH, 4-OH, 5-OCH$_3$ phenyl | 90 | |
| 105 | Cl | H | SO$_2$C$_2$H$_5$ | 2-Cl, 4-OCF$_2$H phenyl | | |
| 106 | Cl | H | SO$_2$CH$_3$ | 2-OCH$_3$, 4-CH$_3$, 5-CH$_3$ phenyl | 141–143 | |
| 107 | H | COOC$_2$H$_5$ | CN | 2,5-dioxo-3,5-dimethyl cyclohexadienyl | | |
| 108 | OCH$_3$ | H | CF$_3$ | 2-Cl, 4-OCF$_2$H, 5-Cl phenyl | | |

TABLE 1-continued

Compounds of the formula (I) according to the invention

| No. | R¹ | R² | R³ | Q | M.p. [°C.] | IC₅₀ |
|-----|-----|-----|-----|---|------------|------|
| 109 | Cl | H | SO₂CH₃ | 2,3-difluoro-6-methyl-phenol | 171–175 | <10⁻⁸ |
| 110 | H | COOC₂H₅ | CF₃ | 2,5-dichloro-3-ethoxy-methylphenyl | | |
| 111 | CCl₃ | Cl | Cl | 2,5-dichloro-4-methyl-phenyl-SO₂—NHCH₃ | | |
| 112 | CCl₃ | Cl | Cl | 3,4-dimethylphenyl-SO₂—NHCH₃ | | |
| 113 | CF₃ | OCH₃ | Cl | 2-methyl-5-hydroxy-phenyl-SO₂—NHCH₃ | | |
| 114 | Cl | H | SO₂CH₃ | 3-methyl-4-hydroxy-phenyl-NH-C(O)CH₃ | 234–235 | 9.0 × 10⁻⁹ |

TABLE 1-continued

Compounds of the formula (I) according to the invention (I)

| No. | R¹ | R² | R³ | Q | M.p. [° C.] | IC$_{50}$ |
|---|---|---|---|---|---|---|
| 115 | Cl | H | SO$_2$CH$_3$ | 2-OCH$_3$-3,4-diCl-phenyl | 98–100 | |
| 116 | Cl | Cl | Br | 2-CH$_3$-4-OCH$_3$-5-Br-6-OCF$_2$H-pyrimidinyl | | |
| 117 | CN | H | Cl | 2-CH$_3$-4-Cl-6-OCF$_2$H-pyrimidinyl | | |
| 118 | Cl | CF$_3$ | Cl | 2-F-3-Cl-5-OCF$_2$H-phenyl | | |
| 119 | NO$_2$ | OC$_2$H$_5$ | Cl | 3-Cl-4-OCF$_2$H-phenyl | | |
| 120 | Cl | H | SO$_2$CH$_3$ | 2-OH-4-F-phenyl | 182–187 | <10⁻⁹ |
| 121 | F | OCH$_3$ | F | 2,3-diCl-4-NO$_2$-phenyl | | |

TABLE 1-continued

Compounds of the formula (I) according to the invention (I)

| No. | R¹ | R² | R³ | Q | M.p. [° C.] | IC$_{50}$ |
|---|---|---|---|---|---|---|
| 122 | Cl | Cl | Cl | 2-methyl-3,5-dihydroxy-5-nitrophenyl | | |
| 123 | CF$_3$ | COOCH$_3$ | Cl | 4-methyl-2-chloro-1-(OCF$_2$H)phenyl | | |
| 124 | Cl | H | SO$_2$CH$_3$ | 2,3-dichloro-6-methylphenyl acetate | 188–192 | |
| 125 | Cl | COOC$_2$H$_5$ | Cl | 2-methyl-5-trifluoromethylphenol | | |
| 126 | NO$_2$ | H | Cl | 2-methyl-3-chloro-5-trifluoromethylphenol | | |
| 127 | Cl | H | SO$_2$CH$_3$ | 2,4-dimethyl-6-methoxy-3-methylphenyl | 136–140 | |
| 128 | OH | CF$_2$H | Br | 2-fluoro-6-methyl-3-chlorophenyl | | |

TABLE 1-continued

Compounds of the formula (I) according to the invention

| No. | R¹ | R² | R³ | Q | M.p. [°C.] | IC$_{50}$ |
|---|---|---|---|---|---|---|
| 129 | F | CH$_3$ | SO$_2$CH$_3$ | 2-methyl-4-trifluoromethylphenol | | |
| 130 | Cl | H | SO$_2$CH$_3$ | 2-methyl-4,6-dichlorophenol | 198–202 | 1.0 × 10⁻⁹ |
| 131 | Cl | H | CF$_3$ | 2-fluoro-3,4-dimethoxy-6-methylphenyl | | |
| 132 | Cl | H | Cl | 3-chloro-4-methyl-1-acetylpyrrole | | |
| 133 | H | Cl | Cl | 2-chloro-3-methoxy-5-methyl-1-acetylpyrrole | | |
| 134 | Cl | H | SO$_2$CH$_3$ | 2-methyl-4,5-dihydroxyphenol | 278 | |
| 135 | Cl | OC$_2$H$_5$ | C$_2$F$_5$ | 2,4,6-trifluoro-3-methylphenyl | | |

TABLE 1-continued
Compounds of the formula (I) according to the invention
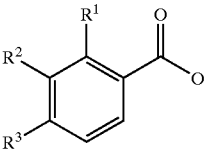
| No. | R¹ | R² | R³ | Q | M.p. [° C.] | IC$_{50}$ |
|---|---|---|---|---|---|---|
| 136 | Cl | H | SO$_2$CH$_3$ | 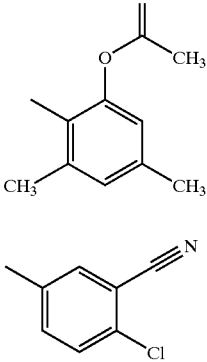 | 105–108 | 3.0 × 10$^{-7}$ |
| 137 | C$_2$F$_5$ | COOCH$_3$ | Cl | 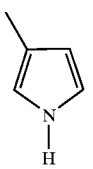 | | |
| 138 | Cl | H | Cl | 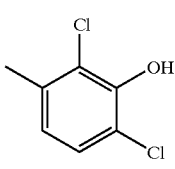 | 173 | |
| 139 | CN | F | Cl | 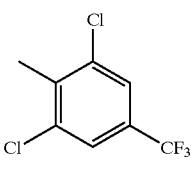 | | |
| 140 | H | Cl | SO$_2$CH$_3$ | 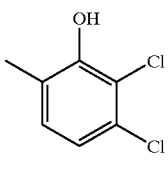 | | |
| 141 | Cl | H | SO$_2$CH$_3$ | 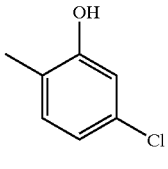 | 182–185 | 1.1 × 10$^{-9}$ |
| 142 | Cl | CF$_2$H | SO$_2$C$_2$H$_5$ |  | | |

TABLE 1-continued

Compounds of the formula (I) according to the invention (I)

| No. | R¹ | R² | R³ | Q | M.p. [° C.] | IC$_{50}$ |
|---|---|---|---|---|---|---|
| 143 | OC$_2$H$_5$ | COOCH$_3$ | SO$_2$CH$_3$ | 2-Cl, 4-OH phenyl | | |
| 144 | CF$_3$ | Cl | SO$_2$CH$_3$ | 2-OH, 5-Cl phenyl | | |
| 145 | NO$_2$ | Cl | OCF$_2$H | 3-NO$_2$, 4-OC$_2$H$_5$, 5-F phenyl | | |
| 146 | Cl | H | Cl | 2,4,5-triOH phenyl | 178 | |
| 147 | CH$_2$Cl | Cl | SO$_2$CH$_3$ | 2-Cl, 4-OH phenyl | | |
| 148 | Cl | H | SO$_2$CH$_3$ | 2-Cl, 4-OH, 5-CH$_3$ phenyl | 193–195 | 9.2 × 10$^{-7}$ |
| 149 | CF$_2$H | H | OCF$_3$ | 3-OH, 5-Cl phenyl | | |

TABLE 1-continued

Compounds of the formula (I) according to the invention (I)

| No. | R¹ | R² | R³ | Q | M.p. [°C.] | IC$_{50}$ |
|---|---|---|---|---|---|---|
| 150 | Cl | H | Cl | 2-methyl-1-(phenylsulfonyl)pyrrole | 122 | |
| 151 | F | CF$_3$ | F | 2,3-dichloro-4-hydroxyphenyl | | |
| 152 | Cl | H | SO$_2$CH$_3$ | 2-hydroxy-3,5,6-trichlorophenyl | 143–144 | $1.2 \times 10^{-7}$ |
| 153 | Cl | Cl | Cl | 2,5-dichloro-3-(methoxycarbonyl)phenyl | | |
| 154 | Cl | COOCH$_3$ | CF$_3$ | 3-chloro-5-hydroxyphenyl | | |
| 155 | C$_2$F$_5$ | H | NO$_2$ | 2,3-dichloro-4-methoxyphenyl | | |
| 156 | Cl | H | SO$_2$CH$_3$ | 2,3-difluoro-4-hydroxyphenyl | 160–165 | $<10^{-9}$ |

TABLE 1-continued

Compounds of the formula (I) according to the invention (I)

| No. | R¹ | R² | R³ | Q | M.p. [° C.] | IC$_{50}$ |
|---|---|---|---|---|---|---|
| 157 | CF$_3$ | H | F | 3-chloro-5-(N-methylsulfamoyl)phenyl | | |
| 158 | Cl | CF$_2$H | SO$_2$C$_2$H$_5$ | 4-chloro-2-methoxyphenyl (with methyl) | | |
| 159 | C$_2$F$_5$ | H | Cl | 2-chloro-3-methyl-6-(methoxycarbonylmethyl)phenyl | | |
| 160 | Cl | H | SO$_2$CH$_3$ | 2-hydroxy-3,5-dimethyl-6-methylphenyl | 142–145 | 2.3 × 10$^{-7}$ |
| 161 | CCl$_3$ | H | SO$_2$CH$_3$ | 2,3-dichloro-5,6-difluoro-4-methylphenyl | | |
| 162 | Cl | CF$_3$ | Cl | 4-chloro-2,5-dimethoxy-6-methylphenyl | | |
| 163 | Cl | H | SO$_2$CH$_3$ | 2,3-dichloro-4-hydroxy-6-methylphenyl | 167–170 | 1.2 × 10$^{-8}$ |

TABLE 1-continued

Compounds of the formula (I) according to the invention (I)

| No. | R¹ | R² | R³ | Q | M.p. [° C.] | IC$_{50}$ |
|-----|-----|------|---------|---|-------------|-----------|
| 164 | Br | OCF₂H | CF₃ | (2-methyl-4-chloro-1-methoxyphenyl) | | |
| 165 | Cl | OCH₃ | SO₂CH₃ | (1-acetyl-2-chloro-3-methoxy-5-methylpyrrole) | | |
| 166 | Cl | H | SO₂CH₃ | (3-fluoro-4-methyl-phenol) | 154–155 | 2.0 × 10⁻⁸ |
| 167 | H | F | CCl₃ | (3-fluoro-4-methyl-phenol) | | |
| 168 | Cl | H | SO₂CH₃ | (2-(2-oxopropyl)-3,6-diacetoxy-methylphenyl) | 161 | |
| 169 | CH₂CF₃ | Cl | Cl | (4-chloro-3-methylbenzoic acid) | | |

TABLE 1-continued

Compounds of the formula (I) according to the invention (I)

| No. | R¹ | R² | R³ | Q | M.p. [° C.] | IC$_{50}$ |
|-----|-----|-----|-----|---|------|------|
| 170 | CF$_2$H | OCH$_3$ | CN | (2-OCH$_3$, 4-Cl, 5-OCH$_3$ phenyl) | | |
| 171 | Cl | H | SO$_3$CH$_3$ | (2-OH, 4-CH$_3$, 5-CH$_3$ phenyl) | 228–230 | 2.2 × 10$^{-8}$ |
| 172 | CF$_3$ | H | Cl | (2-F, 3-Cl, 5-Cl phenyl) | | |
| 173 | Cl | H | Cl | (2-OH, 3-OH, 4-OH phenyl) | 92 | |
| 174 | Br | OCF$_3$ | CH$_2$Cl | (3-Cl, 4-COOH phenyl, with CH$_3$) | | |
| 175 | Cl | H | SO$_2$CH$_3$ | (4-OH phenyl) | 195–196 | 1.2 × 10$^{-8}$ |
| 176 | OH | COOC$_2$H$_5$ | CF$_2$H | (2-F, 3-OH phenyl) | | |

TABLE 1-continued

Compounds of the formula (I) according to the invention (I)

| No. | R¹ | R² | R³ | Q | M.p. [° C.] | IC₅₀ |
|---|---|---|---|---|---|---|
| 177 | H | OCH₃ | F | 2-methyl-5-trifluoromethyl-nitrobenzene group | | |
| 178 | Cl | H | SO₂CH₃ | 2-methyl-5-trifluoromethyl-nitrobenzene group | 118–120 | $4.0 \times 10^{-9}$ |
| 179 | Br | OCH₃ | CF₃ | 3-chloro-6-(chloromethyl)-2-hydroxy-4-methylphenyl group | | |
| 180 | NO₂ | COOCH₃ | OCF₂H | 4-chloro-6-methoxy-2-methylpyrimidine group | | |
| 181 | Cl | H | Cl | 2,4-diacetoxy-5-methoxy-methylphenyl group | 134 | |
| 182 | CN | F | CH₂CF₃ | 4-chloro-3-methyl-benzoic acid group | | |
| 183 | Cl | H | SO₂CH₃ | 3,5-dichloro-2-methyl-phenol group | 123–125 | $4.8 \times 10^{-9}$ |

TABLE 1-continued
Compounds of the formula (I) according to the invention
(I)
| No. | R¹ | R² | R³ | Q | M.p. [° C.] | IC$_{50}$ |
|---|---|---|---|---|---|---|
| 184 | Br | OCH$_3$ | CF$_2$H | 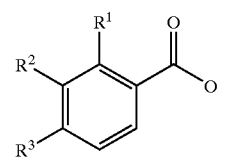 | | |
| 185 | Cl | OCF$_2$H | NO$_2$ | 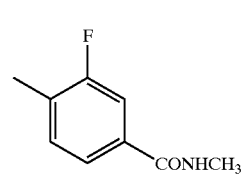 | | |
| 186 | OC$_2$H$_5$ | COOC$_2$H$_5$ | Cl | 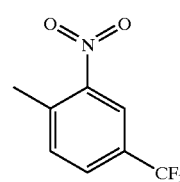 | | |
| 187 | Cl | H | SO$_2$CH$_3$ | 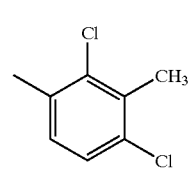 | 117–121 | $4.0 \times 10^{-7}$ |
| 188 | F | Cl | CCl$_3$ | 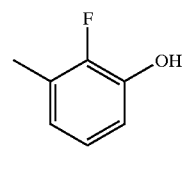 | | |
| 189 | Cl | H | Cl | 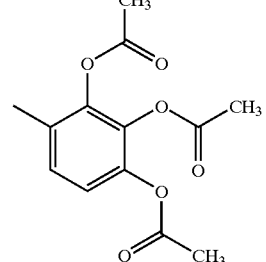 | 101 | |
| 190 | Cl | OCF$_3$ | SO$_2$CH$_3$ | 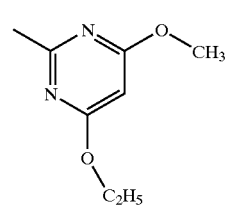 | | |

TABLE 1-continued

Compounds of the formula (I) according to the invention

| No. | R¹ | R² | R³ | Q | M.p. [° C.] | IC$_{50}$ |
|---|---|---|---|---|---|---|
| 191 | Cl | H | SO$_2$CH$_3$ | 4-methyl-3-fluoro-phenol (2-OH, 5-F, methyl) | 164–166 | <10$^{-8}$ |
| 192 | Br | OH | CF$_3$ | 5-methyl-2-chloro-phenyl SO$_3$—CH$_3$ | | |
| 193 | OH | Cl | Cl | 4-chloro-methylphenyl | 116–118 | |
| 194 | Cl | Cl | OH | 4-isopropyl-methylphenyl | 69–71 | |
| 195 | Br | H | CCl$_3$ | 3-chloro-4-(OCF$_2$H)-2-methyl-1-acetyl-pyrrole | | |
| 196 | Cl | H | SO$_2$CH$_3$ | 2-methylphenol | 162–168 | <10$^{-9}$ |
| 197 | F | H | Br | 3-fluoro-2-OH-4-methyl-CONHCH$_3$ phenyl | | |

TABLE 1-continued

Compounds of the formula (I) according to the invention (I)

| No. | R¹ | R² | R³ | Q | M.p. [° C.] | IC$_{50}$ |
|---|---|---|---|---|---|---|
| 198 | Cl | H | Cl | (2-methyl-4,5-bis(acetoxy)phenyl acetate) | 132 | |
| 199 | Cl | Br | CF$_3$ | (3,5-dichloro-4-methylphenyl COOC$_2$H$_5$) | | |
| 200 | Cl | H | Cl | (2-methyl-3,4-dimethoxyphenol) | 135 | |
| 201 | Cl | H | SO$_2$CH$_3$ | (2-hydroxy-5-methylphenyl) | 115–118 | <10$^{-9}$ |
| 202 | F | COOCH$_3$ | SO$_2$CH$_3$ | (2,6-dimethylbenzoquinone) | | |
| 203 | CH$_2$CF$_3$ | H | Br | (3,5-dichloro-4-methyl-CF$_3$ phenyl) | | |

TABLE 1-continued

Compounds of the formula (I) according to the invention (I)

| No. | R¹ | R² | R³ | Q | M.p. [° C.] | IC$_{50}$ |
|---|---|---|---|---|---|---|
| 204 | Cl | H | SO$_2$CH$_3$ | (2-Cl, 4-Cl, methyl-substituted phenyl) | 118–121 | <10$^{-5}$ |

The invention furthermore relates to the use of the herbicidal active substances identified by means of the assay method according to the invention in plant populations.

Suitable plant populations are, in particular, crop plants.

In the examples which follow, the invention is described further and illustrated in greater detail with the aid of examples. Percentages are by weight unless otherwise specified.

EXAMPLE 1

Enriching HPPD from Maize Plants

To enrich the anabolic HPPD from plant tissues, young etiolated maize plants were homogenized in extraction buffer (20 mM phosphate buffer pH 7.0; 0.14 M KCl; 0.1 mg/ml glutathione and 1% insoluble polyvinylpyrrolidone) for 3×10 seconds, for example in a Waring blender. The extract was filtered (all other isolation steps were carried out at 4° C.) and centrifuged (20 minutes; 10,000 g). The supernatant was subjected to fractional ammonium sulfate precipitation. At from 20 to 40% saturation of the solution with ammonium sulfate, HPPD precipitated. At this stage, it was possible to store the enzyme at −80° C. following dialysis in a suitable buffer, such as, for example, 20 mM phosphate buffer pH 7.0; 0.14 M KCl; 0.1 mg/ml glutathione. This degree of purity of the enzyme is sufficient for identifying inhibitors.

EXAMPLE 2

Method for the Identification of Potential HPPD Inhibitors

The enzyme assays were performed in 20 ml polyethylene screw-top containers. Two hypodermic needles (0.9×40 mm) were pushed through the screw-top cap. One of the hypodermic needles was bent to form a hook onto which a small filter paper disk of diameter 10 mm was placed. The filter paper was moistened with 25 µl of methylbenzethonium hydroxide (Sigma). The second hypodermic needle was used for injecting start and stop solution into the screw-top container.

The enzyme reaction mix contained:

1 ml of 0.1 M phosphate buffer, pH 7.3;
2 g/l of bovine liver catalase;
100 µl of a mixture of 3 mM dichlorophenol-indophenol and
150 mM glutathione (reduced);
25 µl of acetone (or potential inhibitors dissolved in acetone) and
enzyme in a total volume of 1,635 µl.

After preincubation for 5 minutes at 30° C., the reaction was started by injecting 800 µl of $^{14}$C-p-hydroxyphenylpyruvate. The reaction was stopped by injecting 600 µl of 1 N H$_2$SO$_4$, incubation was continued for 15 minutes, and the radioactivity which was liberated was determined on the small filter paper disks in a liquid scintillation counter.

EXAMPLE 3

Demonstration of the Inhibition of Plastoquinone Biosynthesis in Wheat by SC-0051

Thin-layer chromatography analysis of the incorporation of radioactivity from $^{14}$C-tyrosine into plastoquinone. Wheat plants were either not treated (A), or sprayed with a standard screening formulation (B) or with 100 g/ha of SC-0051 in this screening formulation (C), and then incubated with $^{14}$C-tyrosine. The lipophilic metabolites of the wheat were extracted using chloroform, separated on silica gel 60 HPTLC plates using chloroform: diethyl ether (99:1), and the radioactivity was analyzed by thin-layer scanner. The incorporation of radioactivity from tyrosine into plastoquinone (see FIG. 1, band 2) can be seen clearly in the control batches (A) and (B), while plastoquinone biosynthesis is inhibited by the use of SC-0051 (C).

EXAMPLE 4

Inhibition of Partially Purified Maize HPPD by the Herbicide SC-0051

The test was carried out analogously to Example 3, but a different inhibitor which also results in bleaching symptoms was used (clomazone). While SC-5001 shows a marked inhibition of HPPD (○), the other bleaching herbicide has no inhibitory action on HPPD (•) (see FIG. 2).

EXAMPLE 5

Demonstration of the Correlation Between HPPD Inhibition and Herbicidal Activity HPPD catalyzes the transformation of p-hydroxyphenylpyruvate to homogentisic acid. If HPPD inhibition is responsible for the herbicidal activity of an inhibitor, then it should be possible to neutralize the herbicidal effect by supplementation with homogentisic acid. This was demonstrated by an experiment with the dockweed *Lemna gibba*. The plant was grown in a sterile aqueous medium supplemented as described in Table 1.

TABLE 1

Neutralization of the effect of SC-0051 by homogentisic acid

| Supplementation of the medium | Number of *L. gibba* plants | |
|---|---|---|
| | Control | $10^{-7}$ M SC-0051 |
| — | 25 | 3 |
| 1 mM HPPD | 22 | 2 |
| 1 mM HGA | 29 | 32 |

Batches of three Lemna plants in 100 ml of sterile medium were incubated for six days with sterile-filtered supplements. SC-0051 was added in the form of a $10^{-3}$ M stock solution (active substance in acetone). The number of newly formed plants was determined on day six.

EXAMPLE 6

Effect of Benzophenones

| Example No. from Table I | $IC_{50}$ value (M) | Growth inhibition of Lemna (%) | | |
|---|---|---|---|---|
| | | $10^{-4}$ M | $10^{-5}$ M | $10^{-6}$ M |
| 183 | $4.8 \times 10^{-9}$ | 98 | 82 | 81 |
| 160 | $2.3 \times 10^{-7}$ | 80 | 72 | 12 |
| 204 | $> 10^{-5}$ | 28 | 12 | — |
| 171 | $2.2 \times 10^{-8}$ | 98 | 93 | 93 |
| 100 | $6.2 \times 10^{-9}$ | 98 | 96 | 92 |

Table 2 shows $IC_{50}$ values of p-hydroxyphenylpyruvate dioxygenase inhibition by a range of benzophenone derivatives in comparison with growth inhibition of *Lemna gibba*.

The $IC_{50}$ value is the molar concentration of the inhibitor at which 50% of the enzyme activity are inhibited. The growth of Lemna was measured as described in: Schulz, A., Ort, O., Beyer, P. and Kleinig, H.; SC-0051, a 2-benzoylcyclohexane-1,3-dione bleaching herbicide, is a potent inhibitor of the enzyme p-hydroxyphenylpyruvate dioxygenase. FEBS-Letters, 1993, 318 (2), 162–166.

It can be seen from this table that the herbicidal activity of the benzophenone derivatives is correlated with the in vitro activity.

What is claimed is:

1. A method for inhibiting p-hydroxyphenylpyruvate dioxygenase of a plant which comprises:
   identifying an inhibitor of p-hydroxyphenylpyruvate dioxygenase of the plant by an assay for identifying inhibitors of anabolic p-hydroxyphenylpyruvate dioxygenase from plants, said assay comprising the steps of:
   incubating an isolated p-hydroxyphenylpyruvate dioxygenase from the plant with a potential inhibitor and,
   after a suitable substrate reaction time, determining the enzymatic activity of the p-hydroxyphenylpyruvate dioxygenase from the plant incubated with the potential inhibitor in comparison with the enzymatic activity of p-hydroxyphenylpyruvate dioxygenase from the plant which has not been so incubated with the potential inhibitor, whereby a decrease in enzymatic activity of the p-hydroxyphenylpyruvate dioxygenase from the plant incubated with the potential inhibitor identifies that the potential inhibitor is an inhibitor of the plant p-hydroxyphenylpyruvate dioxygenase; and
   applying to the plant the identified inhibitor of the p-hydroxyphenylpyruvate dioxygenase of the plant.

2. A method for inhibiting p-hydroxyphenylpyruvate dioxygenase of a plant which comprises applying an inhibitor of p-hydroxyphenylpyruvate dioxygenase to the plant, wherein the inhibitor is identified by an assay for identifying inhibitors of anabolic p-hydroxyphenylpyruvate dioxygenase from plants, which assay comprises:
   incubating an isolated p-hydroxyphenylpyruvate dioxygenase from a plant with a potential inhibitor and,
   after a suitable substrate reaction time, determining the enzymatic activity of the p-hydroxy-phenylpyruvate dioxygenase from a plant incubated with the potential inhibitor in comparison with the enzymatic activity of p-hydroxyphenylpyruvate dioxygenase from a plant which has not been so incubated with the potential inhibitor, whereby a decrease in enzymatic activity of the p-hydroxyphenylpyruvate dioxygenase from a plant incubated with the potential inhibitor indicates that the potential inhibitor is an inhibitor of a plant p-hydroxyphenylpyruvate dioxygenase.

3. A method for inhibiting p-hydroxyphenylpyrdvate dioxygenase of undesired plants and thereby having a herbicidal effect on the undesired plants which comprises:
   identifying an inhibitor of p-hydroxyphenylpyruvate dioxygenase of the plants by an assay for identifying inhibitors of anabolic p-hydroxyphenylpyruvate dioxygenase from plants, said assay comprising the steps of;
   incubating an isolated p-hydroxyphenylpyruvate dioxygenase from a plant with a potential inhibitor and,
   after a suitable substrate reaction time, determining the enzymatic activity of the p-hydroxyphenylpyruvate dioxygenase from the plant incubated with the potential inhibitor in comparison With the enzymatic activity of p-hydroxyphenylpyruvate dioxygenase from the plant which has not been so incubated with the potential inhibitor, whereby a decrease in enzymatic activity of the p-hydroxyphenylpyruvate dioxygenase from the plant incubated with the potential inhibitor identifies that the potential inhibitor is an inhibitor of the plant p-hydroxyphenylpyruvate dioxygenase; and
   applying to the plants or areas in which they grow a herbicidally effective amount of the identified inhibitor of the p-hydroxyphenylpyruvate dioxygenase of the plant.

4. A method for inhibiting p-hydroxyphenylpyruvate dioxygenase of undesired plants and thereby having a herbicidal effect on the undesired plants which comprises:
   applying a herbicidally effective amount of inhibitor of p-hydroxyphenylpyruvate dioxygenase to the plants or areas in which they grow, wherein the inhibitor is identified by an assay for identifying inhibitors of anabolic p-hydroxyphenylpyruvate dioxygenase from plants, which assay comprises:
   incubating an isolated p-hydroxyphenylpyruvate dioxygenase from a plant with a potential inhibitor and, after a suitable substrate reaction time, determining the enzymatic activity of the p-hydroxy-phenylpyruvate dioxygenase from the plant incubated with the potential inhibitor in comparison with the enzymatic activity of p-hydroxyphenylpyruvate dioxygenase from a plant which has not been so incubated with the potential inhibitor, whereby a decrease in enzymatic activity of the p-hydroxyphenylpyrdvate dioxygenase from the plant incubated with the potential inhibitor indicates that the potential inhibitor is an inhibitor of plant p-hydroxyphenylpyruvate dioxygenase.

* * * * *